(12) United States Patent
Cox et al.

(10) Patent No.: US 6,290,966 B1
(45) Date of Patent: Sep. 18, 2001

(54) DIM MUTANTS OF MYCOBACTERIA AND USE THEREOF

(75) Inventors: Jeffery S. Cox, Larchmont; William R. Jacobs, Jr., City Island, both of NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 09/350,326

(22) Filed: Jul. 9, 1999

(51) Int. Cl.[7] ..................... A61K 39/02; A61K 39/04; G01N 33/573; C12P 21/06; C12N 9/00

(52) U.S. Cl. ..................... 424/200.1; 424/248.1; 435/7.4; 435/7.6; 435/7.91; 435/69.1; 435/183; 435/252.3; 435/253.1

(58) Field of Search ............... 424/200.1, 248.1; 435/7.4, 7.6, 7.91, 69.1, 183, 252.3, 253.1

(56) References Cited

PUBLICATIONS

Azad, A.K., et al, "Gene knockout reveals a novel gene cluster for the synthesis of a class of cell wall lipids unique to pathogenic mycobacteria", The Journal of Biological Chemistry, vol. 272, No. 27, pp. 16741–16745, Jul. 1997.*

Wiegeshaus, E.H., et al, "Evaluation of the protective potency of new tuberculosis vaccines", Reviews of Infectious Diseases, vol. 11, Suppl. 2, pp. S484–S490, Mar. 1989.*

* cited by examiner

*Primary Examiner*—Rodney P. Swart
(74) *Attorney, Agent, or Firm*—Amster, Rothstein & Ebenstein

(57) ABSTRACT

Disclosed are novel recombinant mutant strains of mycobacteria that are deficient for the synthesis or transport of dimycoserosalphthiocerol ("DIM"). The present invention also provides a method of producing a recombinant mutant mycobacterium that is deficient for the synthesis or transport of DIM, comprising mutating a nucleic acid responsible for the synthesis or transport of dimycoserosalphthiocerol, including a nucleic acid comprising the promoter for the pps operon, fadD28 or mmpL7. The present invention also provides a vaccine comprising a DIM mutant mycobacterium of the present invention, as well as a method for the treatment or prevention of tuberculosis in a subject using the vaccine.

16 Claims, 6 Drawing Sheets

SEQUENCE LISTING

```
<160> NUMBER OF SEQ ID NOS: 4

<210> SEQ ID NO: 1
<211> LENGTH: 20
<212> TYPE: DNA
<213> ORGANISM: Artificial Sequence
<220> FEATURE:
<221> NAME/KEY: primer
<222> LOCATION:
<223> OTHER INFORMATION: primer o84L-F

<400> SEQUENCE: 1
gtcatccggc tcatcaccag                                              20

<210> SEQ ID NO: 2
<211> LENGTH: 20
<212> TYPE: DNA
<213> ORGANISM: Artificial Sequence
<220> FEATURE:
<221> NAME/KEY: primer
<222> LOCATION:
<223> OTHER INFORMATION: primer o84L-R

<400> SEQUENCE: 2
aactggcgca gttcctctgg                                              20

<210> SEQ ID NO: 3
<211> LENGTH: 22
<212> TYPE: DNA
<213> ORGANISM: Artificial Sequence
<220> FEATURE:
<221> NAME/KEY: primer
<222> LOCATION:
<223> OTHER INFORMATION: primer o84R-F

<400> SEQUENCE: 3
atacacgcgc accggttcta gc                                           22

<210> SEQ ID NO: 4
```

```
<211> LENGTH: 18
<212> TYPE: DNA
<213> ORGANISM: Artificial Sequence
<220> FEATURE:
<221> NAME/KEY: primer
<222> LOCATION:
<223> OTHER INFORMATION: primer o84R-R

<400> SEQUENCE: 4
cacggcgaac cgctggtg                                              18
```

DIM MUTANTS OF MYCOBACTERIA AND USE THEREOF

STATEMENT OF GOVERNMENT INTEREST

This invention was made with government support under NIH Grant No. AI-26170. As such, the United States government has certain rights in this invention.

BACKGROUND OF THE INVENTION

Tuberculosis is the leading cause of death in the world due to a single bacterial infection (27). Despite its enormous burden on world health, little is known about the molecular mechanisms of *M. tuberculosis* pathogenesis. Bacterial multiplication and concomitant tissue damage within an infected host, including experimentally infected mice, occurs primarily in the lungs—the favored niche of *M. tuberculosis* (28). Although it has been postulated that the distinctive cell wall of *M. tuberculosis* is important for virulence, rigorous genetic proof has been lacking. Using signature tagged mutagenesis, the inventors have isolated three attenuated *M. tuberculosis* mutants that are unable to synthesize or transport a complex, cell wall-associated lipid known as dimycoserosalphthiocerol (DIM). Two mutants of the present invention have transposon insertions affecting genes implicated in DIM synthesis, while the third mutant has a disruption of a gene encoding a large transmembrane protein required for DIM secretion. Surprisingly, synthesis and transport of this complex lipid is only required for growth in the lung; all three mutants are unaffected for growth in the liver and spleen. *M. tuberculosis* mutants deficient for DIM synthesis are attractive candidates for the development of a live, attenuated vaccine.

SUMMARY OF THE INVENTION

The present invention provides novel recombinant mutant strains of mycobacteria that are deficient for the synthesis or transport of dimycoserosalphthiocerol ("DIM"). The present invention also provides a method of producing a recombinant mutant mycobacterium that is deficient for synthesis or transport of dimycoserosalphthiocerol, comprising mutating a nucleic acid responsible for the synthesis or transport of dimycoserosalphthiocerol. Methods of producing the recombinant mutant mycobacterium of the present invention include, for example, illegitimate recombination, legitimate recombination and transposon insertion. Further provided by the present invention is a vaccine using the recombinant mutant mycobacterium of the present invention, as well as a method of treating or preventing tuberculosis in a subject comprising administering the vaccine of the present invention in an amount effective to treat or prevent tuberculosis in the subject.

The present invention is described in the following Detailed Description of the Invention which is set forth to aid in the understanding of the invention, and should not be construed to limit in any way the scope of the invention as defined in the claims which follow thereafter.

DETAILED DESCRIPTION OF THE INVENTION

Figure 1A:
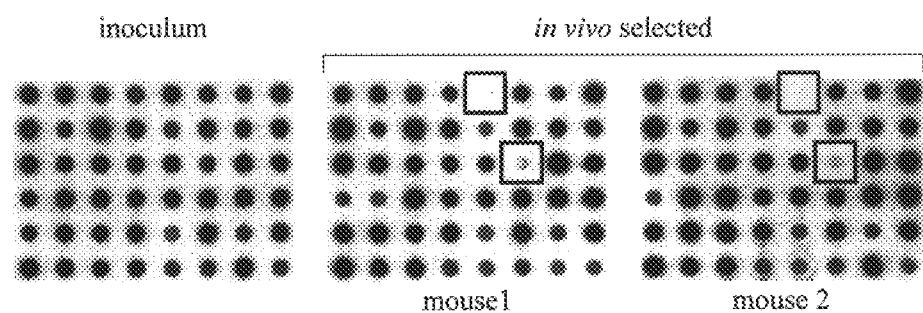
FIG. 1 illustrates three related, avirulent mutants of *M. tuberculosis* isolated by STM mutagenesis. Panel A: 12 pools of 48 transposon mutants were used to infect C57BL/6 mice (2 mice infected per pool). Signature-tags from mycobacteria harvested from the inoculum and the lungs of mice after 3 weeks of growth were amplified, radiolabeled, and hybridized to tag-array filters. Results from one pool are shown and tags from mutants under represented in vivo are boxed. Panel B: A schematic representation of the transposon insertion sites from 3 STM mutants within a 44 kb region of the *M. tuberculosis* genome. Panel C: Wild-type *M. tuberculosis* (mc$^2$3104) and the pps-promoter,fadD28, and mmpL7 mutants (mc$^2$3105, mc$^2$3106, and mc$^2$3107 respectively) were plated for single colonies on solid media and incubated for 4 weeks at 37° C.
Figure 1B:
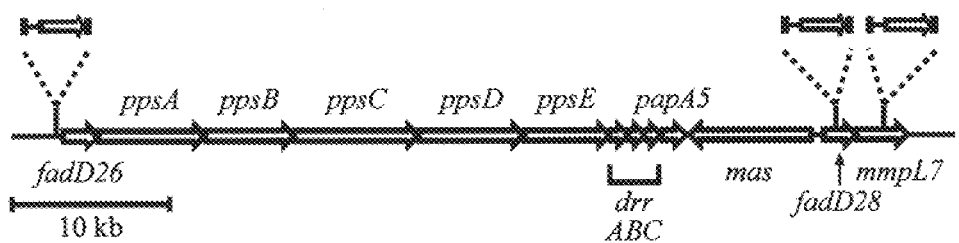
Figure 1C:
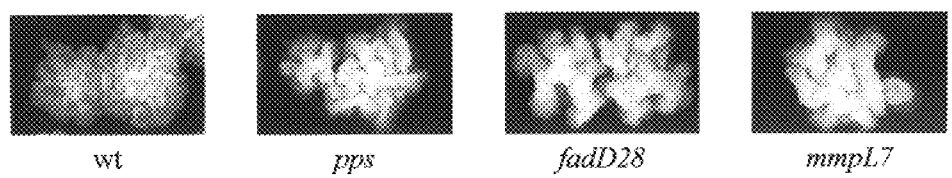

The present invention provides for a recombinant mutant mycobacterium deficient for the synthesis or transport of dimycoserosalphthiocerol. The mutant mycobacterium of the present invention may be any strain of slow-growing mycobacteria normally expressing or transporting DIM in its unmutated state, but is preferably a strain of *M. paratuberculosis, M. microti, M. marinum,* or *M. avium,* and most preferably is a strain of *M. tuberculosis, M. bovis*-BCG, or *M. leprae.* As used herein, "mutant mycobacterium" means that the mycobacterium possesses at least one mutated gene such that the expression or function of the gene is varied with respect to the non-varied gene in the parent strain. The gene may be any gene that is involved in the synthesis, transport or regulation of DIM, including but not limited to one or more of fadD26, ppsA, ppsB, ppsC, ppsD, ppsE, mas, drrA or drrB, or homologues thereof. As used herein, "homologues" are nucleic acids comprising homologous nucleotide sequences and whose expressed product is functionally equivalent. In a preferred embodiment of the invention, the mutation is located in one or more of the promoter region of the pps operon, the fadD28 gene, and/or the mmpL7 gene. Accordingly, in a preferred embodiment of the invention, the recombinant mutant mycobacterium comprises a mutated pps operon, fadD28, or mmpL7 gene. The recombinant mutant mycobacterium comprising a mutated pps operon or a mutated fadD28 gene is deficient in the synthesis of DIM. The recombinant mutant mycobacterium comprising a mutated mmpL7 gene is deficient in the transport of DIM. Mutated genes may comprise deletion, point, substitution, or insertion mutations from the wildtype nucleotide sequence.

The present invention also provides a method of producing a recombinant mutant mycobacterium that is deficient for synthesis or transport of dimycoserosalphthiocerol, which comprises mutating a nucleic acid responsible for the synthesis or transport of dimycoserosalphthiocerol. The methods whereby the recombinant mycobacteria of the present invention are mutated include, for example, methods of illegitimate recombination, legitimate recombination, and transposon insertion. The mycobacterium may be mutated through an insertional mutation of a mycobacterial gene. The insertional mutation of the mycobacterial gene may be effected through illegitimate recombination of DNA into the mycobacterial chromosome, or by homologous recombination, or by the insertion of a mycobacterial transposon into a mycobacterial gene, or by the transfection of a mycobacterium with a vector which includes a pair of inverted repeat sequences and DNA encoding a transposase. In addition, it is also within the confines of the present invention that the recombinant mutant mycobacterium of the present invention that is deficient in the synthesis or transport of DIM may be generated using the methods described in copending U.S. application Ser. No. 08/938,059, filed Sep. 26, 1994, entitled "TM4 Conditional Shuttle Phasmids and Uses Thereof"; copending U.S. application Ser. No. 09/350,048, entitled "One Step Allelic Exchange in Mycobacteria Using In Vitro Generated Conditional Transducing Phages," filed Jul. 8, 1999; and copending U.S. application Ser. No. 09/350,047, entitled "Unmarked Deletion Mutants of Mycobacteria and Methods of Using Same," filed Jul. 8, 1999, the contents of which are hereby incorporated by reference.

The present invention provides a vaccine comprising a recombinant mutant mycobacterium that is deficient for the synthesis or transport of DIM. The invention also provides a method of treating or preventing tuberculosis in a subject comprising administering the vaccine of the present invention in an amount effective to treat or prevent tuberculosis in the subject. In this regard, the vaccine containing the recombinant mutant mycobacterium of the present invention may be administered in conjunction with a suitable physiologically acceptable carrier. Mineral oil, alum, synthetic polymers, etc., are representative examples of suitable carriers. Vehicles for vaccines and therapeutic agents are well within the skill of one skilled in the art. The selection of a suitable vaccine is also dependent upon the manner in which the vaccine or therapeutic agent is to be administered. The vaccine or therapeutic agent may be in the form of an injectable dose and may be administered intramuscularly, intravenously, orally, intradermally, or by subcutaneous administration.

Further, mycobacteria have well known adjuvant properties and so are able to stimulate a subject's immune response to respond to their antigens with great effectiveness. Their adjuvant properties are especially useful in providing immunity against pathogens in cases where cell mediated immunity is critical for resistance. In addition, the mycobacterium stimulates long-term memory or immunity and thus a single inoculum may be used to produce long term sensitization to protein antigens. The vaccine of the present invention may be used to prime long-lasting T-cell memory, which stimulates secondary antibody responses which will neutralize infectious agents or toxins, e.g., tetanus and diptheria toxins, pertussis, malaria, influenza, herpes virus and snake venom.

The present invention is described in the following Experimental Details Section which is set forth to aid in the understanding of the invention, and should not be construed to limit in any way the invention as defined in the claims which follow thereafter.

Experimental Details Section

A. Materials and Methods

Media and Strains. *M. tuberculosis* strains were grown in 7H9 liquid media supplemented with 10% OADC, 0.5% glycerol, and 0.1% Tween-80 or 7H10 solid media with the same supplements except Tween-80. STM media is either 7H9 or 7H10 supplemented with 0.5% casamino acids, 20 mg/ml tryptophan, 10% OADC, 0.5% glycerol, 1 ug/ml cyclohexamide. When added, hygromycin B was at a final concentration of 50 ug/ml. The pps promoter, fadD28, and mmpL7 mutant strains are named $mc^2$3105, $mc^2$3106, and $mc^2$3107 respectively. The wild-type Erdman strain carrying the integrating vector pMV306.hyg (to confer hygromycin resistance) is named $mc^2$3104

STM mutagenesis. The random tag library was constructed exactly as done previously except that a SphI site was introduced at the ends of the tags (1). All amplification, labeling, and hybridization of tags were done as previously described (1). The tags were ligated into the unique SphI site of the Tn5370 transposon (containing the hygromycin resistance gene) in pJSC84 and the resulting plasmids were introduced into the genome of the temperature-sensitive phage phAE87 as described previously (23). 48 phages containing tags that hybridized well to its cognate tag on the array and not to the other 47 tags were selected. Tag arrays were made by applying either amplified tags or phage genomic DNA onto hybond-N+ nylon filters (Amersham Pharmacia Biotech) using a Bio-Dot filter apparatus (Bio-Rad). Transposon mutagenesis of the Erdman strain was performed as done previously using all 48 phages individually (23). Colonies were picked into 48-well plates containing STM liquid media and portions of the cultures were combined to create the inoculum pool, which was subsequently frozen, and titered. 6–8 week old, female C57BL/6 mice (Jackson Labs) were infected by tail vein injection with approximately $3\times10^6$ cfu and the lungs were harvested and homogenized at three weeks post-infection. Total DNA from the homogenate was prepared by boiling and bead-beating in the presence of phenol. The insertion site of the transposon in the selected mutants was determined by sequencing the products of inverse PCR (24). Briefly, 0.5 mg of genomic DNA was digested with RsaI, ligated to form circles, and then genomic sequences flanking both sides of the transposon were amplified. Primers used to amplify from the left side of the transposon were o84L-F (5'-GTCATCCGGCTCATCACCAG-3') (SEQ ID NO:1) and o84L-R (5'-AACTGGCGCAGTTCCTCTGG-3') (SEQ ID NO:2), and the right side was amplified using o84R-F (5'-ATACACGCGCACCGGTTCTAGC-3') (SEQ ID NO:3) and o84R-R (5'-CACGGCGAACCGCTGGTG-3') (SEQ ID NO:4). Finally, DNA from each mutant was subjected to southern analysis using the hygromycin resistance marker gene as a probe to certify that only one transposon was present in the genome.

Biochemical analysis of DIM. Labeling, extraction, and analysis of lipids was done essentially as described previously (5). Actively growing cultures were diluted to $OD_{600}=0.8$ in a final volume of 50 mls. 20 mCi of $Na[1-^{14}C]$ propionate (American Radiolabeled Chemicals) was added and incubation continued for 16 h at 37° C. Cell pellets were washed twice with water and then extracted with 5 mls of chloroform:methanol (2:1) at room temperature overnight. Lipids were prepared by the Folch method (25), dried under nitrogen, and dissolved in 1 ml of ethyl ether. 4 ml was separated on 10 cm×10 cm HPTLC plates (Alltech) using chloroform:methanol (19:1) as the solvent. 5 mg purified DIM (supplied by Dr. P. Brennan) was applied as a marker and visualized by spraying with 20% $H_2SO_4$ in ethanol and charring at 110° C. for 15 min. For pulse-chase experiments, 80 mls of culture was incubated with 32 mCi of $Na[1-^{14}C]$ propionate for 2 h. Cells were centrifuged and washed with fresh media 3 times and resuspended in 80 mls media. 15 ml aliquots were removed at different time points following incubation at 37° C. and cells were pelleted by centrifugation, washed and extracted. Media was filtered through 0.2 mm filters, lyophilized, and then extracted as done for cell pellets.

Infection of individual STM mutants. Actively growing cultures of $mc^2 3104$–3107 were washed and resuspended in 1×PBS, 0.1% Tween-80 and sonnicated. C57BL/6 mice were infected by tail vein injection with $1×10^6$ cfu of each strain using an $OD_{600}=3×10^8$ cfu/ml. Organs from infected mice were homogenized and plated exactly as described earlier (26).

B. Results and Discussion

Figure 2A:
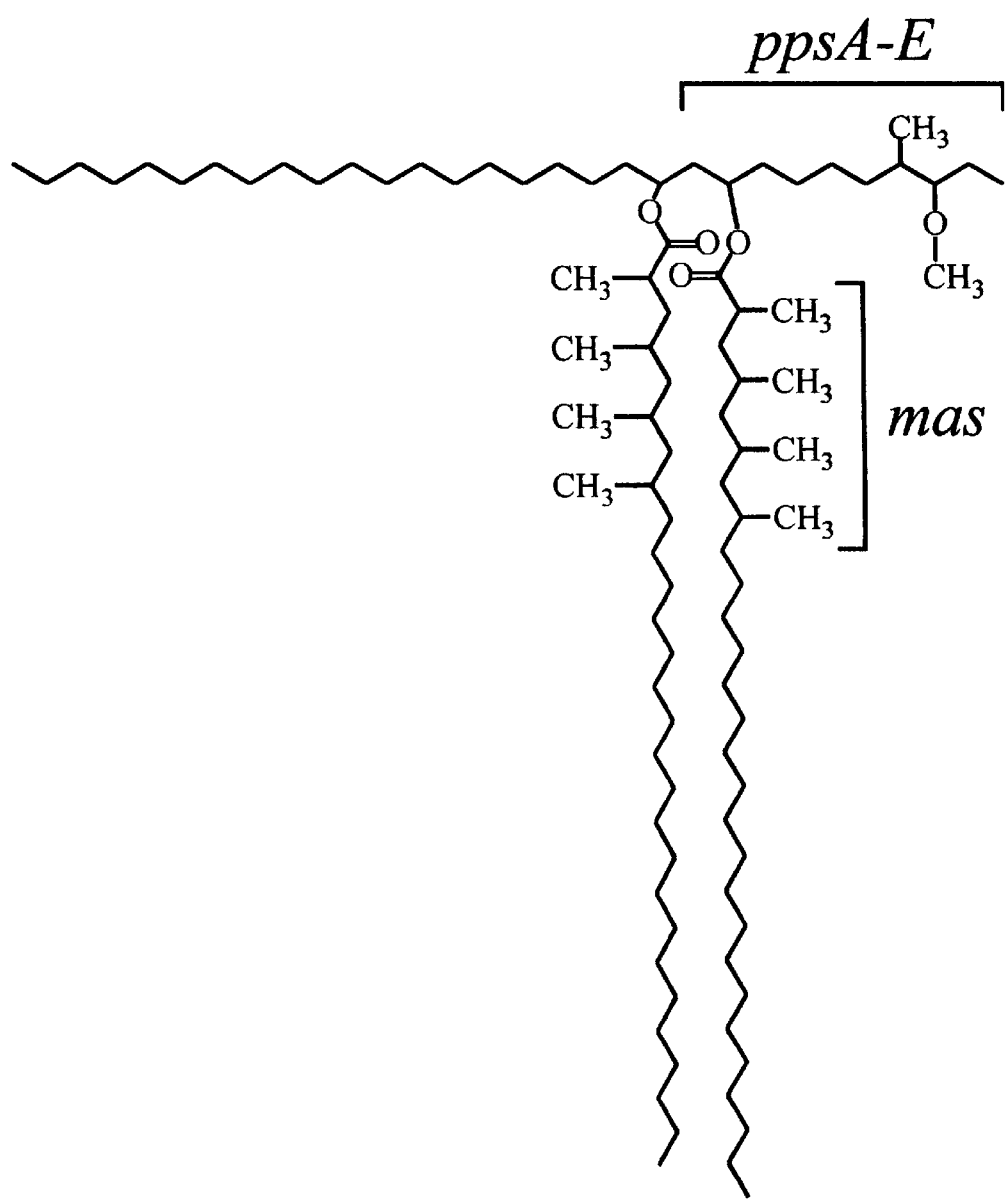
FIG. 2A depicts DIM structure denoting the sites of propionic acid incorporation onto straight-chain fatty acids by the action of the ppsA-E and mas gene products (29).
Figure 2B:
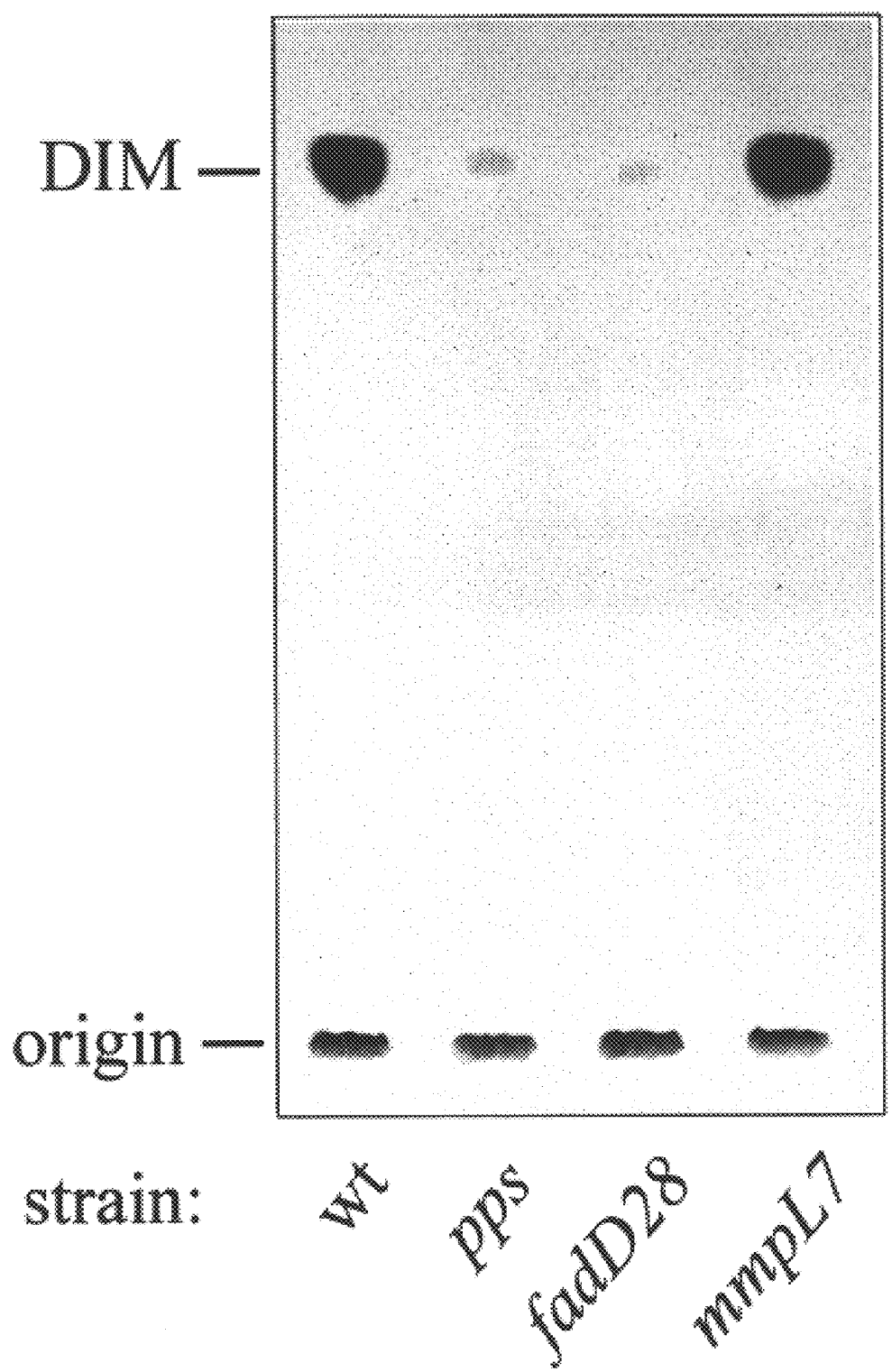
FIG. 2B illustrates DIM in crude lipid extracts from equal numbers of cells labeled with [1–$^{14}$C]propionic acid for 16 h and separated by thin-layer chromatography. The identity of DIM in these extracts was confirmed by co-migration of a purified preparation of authentic DIM.
Figure 2C:
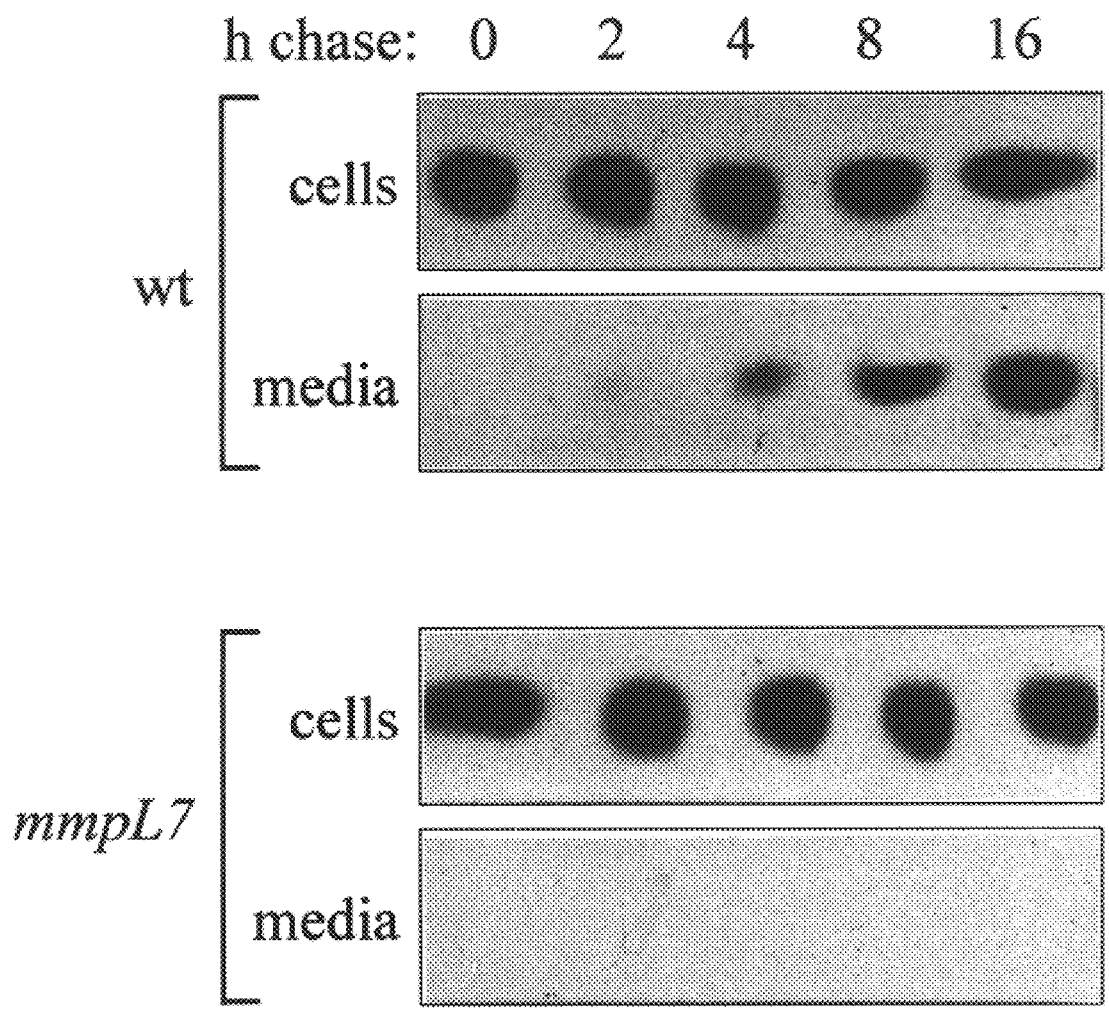
FIG. 2C shows results of pulse-chase analysis. Wild-type and mmpL7 mutant cells were pulse labeled with [1–$^{14}$C] propionic acid for 2 h, washed extensively, and re-incubated in fresh media. Lipid extracts from cell pellets and filtered media were isolated at the denoted time points during the chase period as described in Methods.
Figure 3:
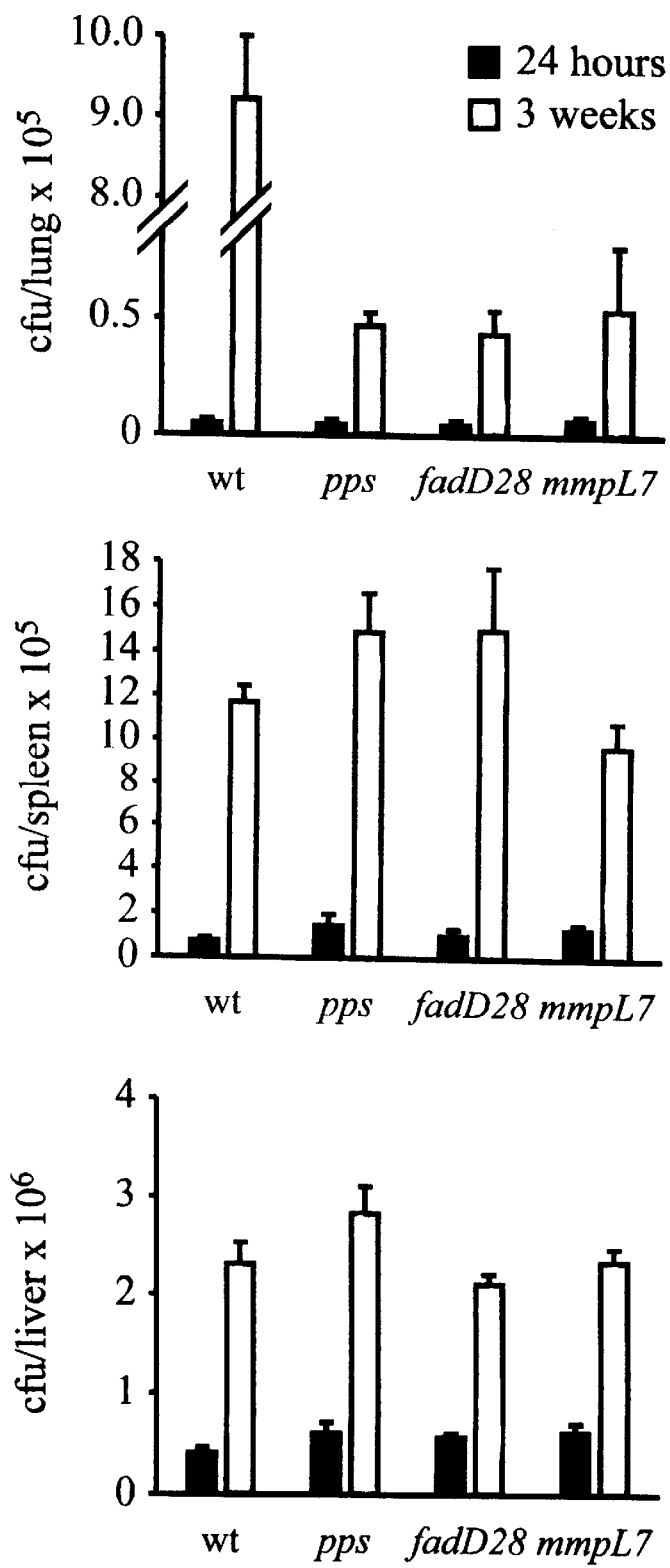
FIG. 3 depicts that DIM synthesis and export is required for *M. tuberculosis* replication in mouse lungs but not in the liver or spleen. Panel A: C57BL/6 mice were infected with 1×10$^6$ cfu of each strain and *M. tuberculosis* cells were harvested from lungs at 24 h (black bars) and 3 weeks (gray bars) post-infection and counted by plating. Error bars represent the standard error from at least 3 experiments. Panels B and C: *M. tuberculosis* cells were harvested and counted from spleens (Panel B) and livers (Panel C) from the same mice described in Panel A.
Figure 4:
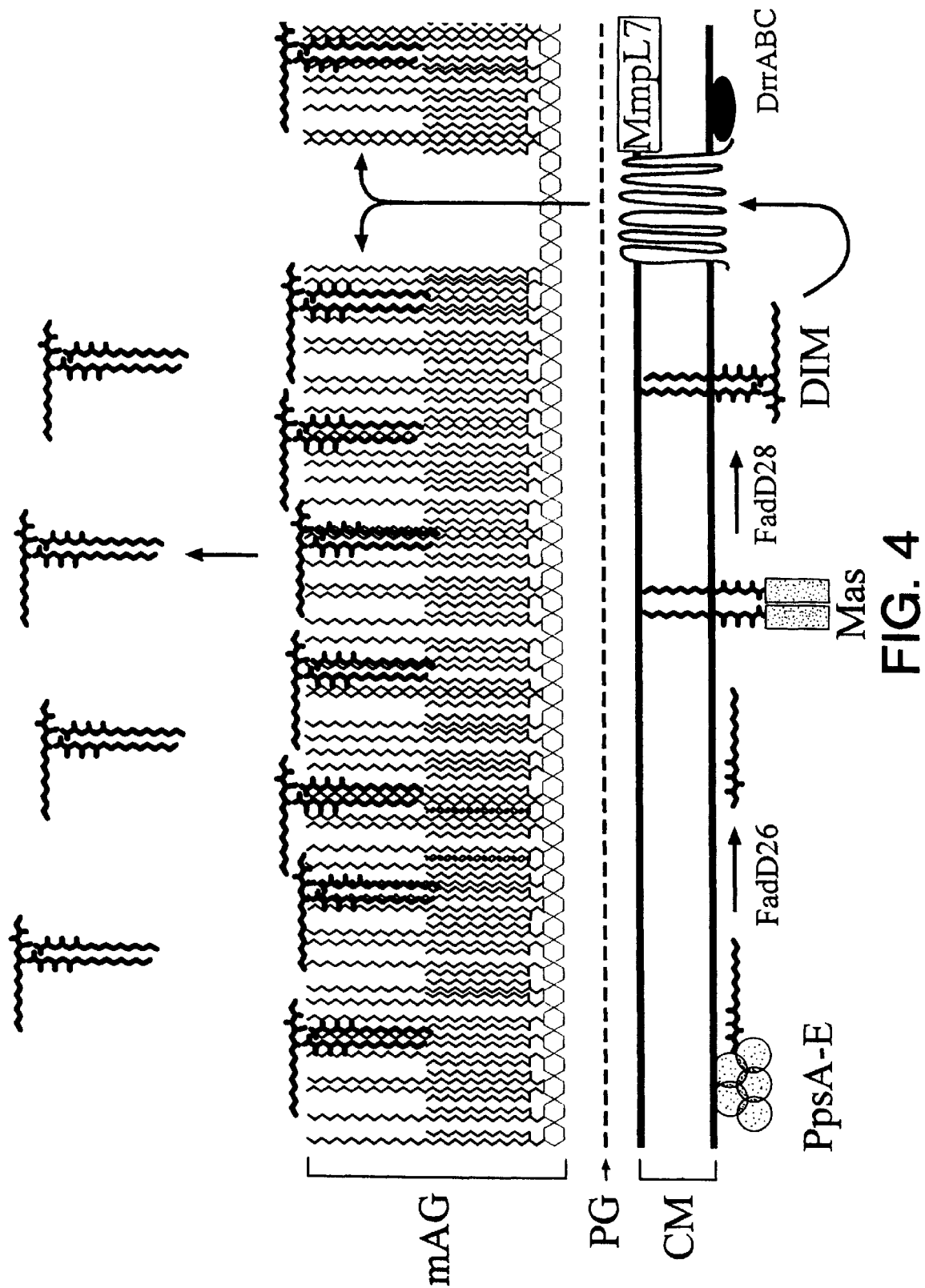
FIG. 4 shows a model for synthesis and export of DIM. Arrows above FadD26 and FadD28 represent acyl-transfer reactions hypothetically catalyzed by these proteins, releasing phthiocerol and mycocerosic acids from their respective synthases (PpsA-E and Mas) and condensing the lipids to form DIM. Once formed, DIM may be transported across the cytoplasmic membrane (CM) by MmpL7—perhaps in concert with the ABC transporter-like DrrAB proteins. Presumably DIM can diffuse through the peptidoglycan (PG) layer and into the lipid-rich mycolylarabinogalactan (mAG) layer of the cell wall.

To identify M tuberculosis genes required for growth in vivo, the inventors adopted the signature-tag mutagenesis (STM) scheme originally used to identify virulence genes in S. typhimurium (1). This approach allows for the screening of pools of random transposon mutants for those variants that are unable to replicate within host tissues. To this end, multiple sets of 48 random transposon mutants of the Erdman strain of M. tuberculosis* were created and grown in 48-well plates such that each mutant within a set contained a unique 80 bp DNA sequence "tag". Using DNA oligonucleotide primers complementary to common sequences adjacent to all 48 tags, each tag could be amplified by PCR, radio-labeled, and distinguished from the other 47 tags by hybridization to an ordered array of the unlabeled DNA tags fixed to a nylon membrane. Significantly, after pooling aliquots of culture from a 48-well plate to create an "inoculum pool", the relative abundance of each individual tag, and thus each *M. tuberculosis* mutant, within each set could be readily assessed by its hybridization signal on the membrane. Therefore, the inventors sought to identify mutants containing tags that were abundant in the inoculum pool but were scarce or absent from the same pool after growth in the lungs of infected mice.

As an initial screen, 12 sets of mutant pools were created and each set was used to infect two immunocompetent C57BL/6 mice by tail vein injection. Each pool was analyzed in two mice in order to control for the possibility of stochastic loss of the tags, increasing confidence that only bona-fide mutants would be identified. After three weeks, mycobacteria were harvested from the lungs of the animals and genomic DNA was prepared. DNA tags from bacilli present in the inoculum pool as well as those grown in vivo were amplified and used as probes on separate tag arrays. FIG. 1, Panel A shows the result of a representative pool in which all of the 48 mutants were present in the inoculum pool (FIG. 1, Panel A, "inoculum") but two mutants were significantly under represented from the lungs of each of the infected mice (FIG. 1, Panel A, "in vivo selected"). Only those mutants whose tags were under represented or missing in both of the infected mice were selected for further study. In total, 14 giv (growth in vivo) mutants were isolated out of 576 transposon-containing isolates screened, a rate (2.4%) similar to that found in STM screens of other bacterial pathogens (0.5–4.0%) (1–3).

The insertion site of the transposon within the genome of each giv mutant was determined and compared to the genomic sequence of *M. tuberculosis*. Interestingly, most of the transposon insertions disrupted open reading frames encoding proteins of unknown function (data not shown). Initial studies focused, therefore, on three giv mutants that had insertions within a 44 kb region containing genes whose products are involved in the synthesis of dimycoserosalphthiocerol (DIM), a cell wall-associated lipid found exclusively in pathogenic mycobacteria (4).

As shown in FIG. 1, Panel B, the first mutant contains a transposon insertion in the promoter region of a large operon that includes the ppsA-E genes. These genes are highly homologous to those encoding the multi-subunit polyketide synthase required for phthiocerol biosynthesis in *M. bovis* BCG (5). (A well studied derivative of phthiocerol, phenolphthiocerol, is also produced by the pps synthase in *M. bovis*, but this lipid is absent in most *M. tuberculosis* strains including the Erdman strain used here.) As expected, the transposon insertion within the *M. tuberculosis* STM mutant vastly reduced transcription of genes within the operon (data not shown). Immediately downstream of the pps operon is the *M. tuberculosis* homologue of the mas gene which in BCG encodes a fatty acid synthase-like enzyme responsible for the synthesis of mycocerosic acids (6, 7). The products of these two synthases are attached covalendy by an unknown mechanism to form DIM (FIG. 2A). The second mutant contains an insertion infadD28, one of 36 homologues of the *E. coli* fadD gene identified in the *M. tuberculosis* genome (8). FadD28, however, is likely involved in acyl transfer of mycocerosic acid instead of fatty acid catabolism as a mutation of the fadD28 homologue in BCG specifically inhibits mycocerosic acid synthesis and thus DIM synthesis (9).

Finally, the third STM mutant has a transposon insertion in the mmpL7 gene which is directly downstream of fadD28. mmpL7 encodes for a transmembrane protein of unknown function but with high homology to a number of proteins encoded by the *M. tuberculosis* genome as well as ActII-ORF3, a membrane protein required for secretion of the antibiotic actinorhodin in *Streptomyces coelicolor* (10). It is important to note that the mmpL7 mutant, like the pps and fadD28 mutants, is specifically defective for in vivo growth as its doubling time in liquid culture is identical to that of the parent Erdman strain (not shown).

The first indication that all three attenuated mutants were defective for cell wall biosynthesis came from the observation that each displayed a strikingly altered colony morphology as compared to wild-type *M. tuberculosis* when grown on solid media (FIG. 1, Panel C). Whereas wild-type cells formed characteristically flat, "corded" colonies, each of the mutant cells produced disorganized colonies that raised above the plane of the agar plate. Colony morphology in *M. tuberculosis* has long been associated with virulence (11, 12). Although surface-exposed lipids have been implicated as key contributors to this phenotype, this is the first demonstration of a link between a specific lipid biosynthetic pathway, colony morphology, and virulence.

Given that all the genes in this region of the *M. tuberculosis* genome are nearly identical to those in BCG, the inventors sought to determine whether these transposon mutants were deficient for DIM synthesis. DIM can be specifically labeled in vivo with $^{14}$C-propionate as it is a precursor to methylmalonyl-CoA, the substrate used by the synthases to introduce methyl branches onto straight-chain fatty acids (13). Therefore, to determine if the three transposon mutants are able to produce DIM, cells were labeled with $^{14}$C-propionate, and whole-cell lipids were extracted and analyzed by thin-layer chromatography (TLC). As shown in FIG. 2B, extracts prepared from wild-type *M. tuberculosis* cells contain substantial amounts of DIM (lane 1). Importantly, extracts prepared from the pps-promoter mutant and the fadD28 mutant contained little to no detectable amount of the lipid (FIG. 2B, lanes 2 and 3). In contrast, mmpL7 mutant cells accumulated large amounts of the labeled lipid (FIG. 2B, lane 4), indicating that mmpL7 is not required for DIM synthesis. Initially, this result was puzzling because the phenotypes of the mmpL7 mutant (inability to grow in vivo, altered colony morphology) were identical to the other two STM mutants that produced no DIM at all. However, the homology between mmpL7 and actII-ORF3 suggested that instead of being required for DIM synthesis, MmpL7 may be involved in DIM export from the cell. To verify this hypothesis, the inventors performed pulse-chase labeling experiments with $^{14}$C-propionate to follow the fate of newly synthesized DIM in both wild-type and mmpL7 mutant cells. As shown in FIG. 2C, a considerable portion of the labeled DIM is exported into the liquid culture medium from wild-type *M. tuberculosis* cells 16 hours after synthesis. To the inventors' knowledge, this is the first demonstration that DIM can be secreted beyond the exterior of the cell wall. In striking contrast, mmpL7 mutant cells were unable to secrete DIM into the culture medium and all of the labeled lipid remained associated with the cell pellet (FIG. 2C, lower panels). In three separate experiments, an average of 45% of the labeled DIM was recovered in the media at 16 hours post-chase from wild-type cultures. DIM secretion was never detected from mmpL7 mutant cultures.

In total, the isolation of these three independent mutants from the STM screen was highly suggestive that DIM production and secretion by *M. tuberculosis* is important for growth in the lungs of the host. However, since these mutants were isolated from pools of infected bacteria, the inventors sought to verify that they were also defective for growth when injected as a clonal population. Therefore, C57BL/6 mice were infected with $1\times10^6$ cfu of either the wild-type Erdman strain or each of the three transposon mutants. As shown in FIG. 3, wild-type *M. tuberculosis* cells were able to replicate extensively in the lungs during the first three weeks after infection, leading to nearly a 200-fold increase in the number of viable mycobacteria recovered from the organ (top panel, wt). However, in mice infected with cells from either the pps-promoter, fadD28, or mmpL7 mutant strains, mycobacterial replication was severely restricted in the lungs (FIG. 3, Panel A). It is notable, however, that although all three mutants were compromised for growth in the lung as compared to wild-type, they were still able to grow slightly in the organ (approx. 8-fold increase). Although replication of wild-type *M. tuberculosis* is greatest in the lung, infection by intravenous injection also leads to the seeding of mycobacterial cells into other organs where they can multiply. To determine the capacity of the three mutants to grow in tissues other than the lung, the inventors monitored the number of mycobacteria in the spleens and livers of the same infected mice used for the experiments described above. Surprisingly, growth of cells from all three mutants were nearly identical to wild-type in both organs (FIG. 3, Panels B and C). This novel result demonstrates that DIM is specifically required for growth in the lungs of infected mice.

Because of the marked tissue-specific growth defect of all three of the DIM mutants, the inventors believe that the DIM biosynthetic and secretory pathway is present to protect *M. tuberculosis* from a lung-specific defense mechanism of the host. Furthermore, the fact that DIM is present on the outermost surface of the bacillus and can be secreted into culture media suggests that it interacts directly with the host immune system (4). This is an appealing model since products of polyketide synthases from other actinomycetes, such as rapamycin, are known to exert immuno-suppressive effects on mammalian immune systems (14). Indeed, a glycosylated version of dimycoserosalphenolphthiocerol purified from *M. leprae* has the capacity to suppress the anti-bacterial respiratory burst in in vitro cultured macrophages as well as to directly scavenge oxygen radicals (15–17). Future experiments will be designed to identify the lung-specific host mechanism(s) responsible for controlling the proliferation of mutants deficient for DIM.

As shown in FIG. 4, DIM synthesis is complex and requires the action of the polyketide synthase-like Pps enzymes, Mas, at least one acyl-CoA synthase-like protein, and MmpL7. Since the mmpL7 mutation affects DIM export, MmpL7 is likely to be involved in the direct transfer of DIM across the cytoplasmic membrane. Interestingly, the sequence of the cluster of genes at the 3' end of the pps operon suggest that DIM export may require proteins in addition to MmpL7 (FIG. 1). Of particular interest are the drrA and drrB genes that encode for an ABC transporter highly homologous to proteins implicated in doxorubicin efflux from *Streptomyces peucetius* (18, 19). Future experiments will address the possibility that DrrA and DrrB may be involved in the export of DIM from the cytoplasmic membrane to the cell wall.

An *M. tuberculosis* mutant unable to synthesize DIM could play an important role in the development of a superior replacement for the currently used BCG vaccine. Although the efficacy of BCG vaccination is variable, it is clear that the vaccine strain must replicate within the host in order to provide protection against tuberculosis (20, 21). Indeed, auxotrophic mutants of *M. tuberculosis* are quickly cleared from all tissues of infected mice and provide uneven protection to subsequent infection with virulent *M. tuberculosis* as compared to BCG vaccination (22). Although safety of a *M. tuberculosis* strain deficient only in DIM is a concern, current experiments are underway to determine if such mutants have the ability to create a sustained antigenic stimulus required for a robust, protective immune response.

References

1. Hensel, M., et al. *Science* 269, 400–3 (1995).
2. Chiang, S. L. & Mekalanos, J. J. *Molecular Microbiology* 27, 797–805 (1998).
2. Chiang, S. L. & Mekalanos, J. J. *Molecular Microbiology* 27, 797–805 (1998).
3. Mei, J. M., Nourbakhsh, F., Ford, C. W. & Holden, D. W. *Mol Microbiol* 26, 399–407 (1997).
4. Brennan, P. J. & Nikaido, H. *Annual Review of Biochemistry* 64, 29–63 (1995).
5. Azad, A. K., Sirakova, T. D., Fernandes, N. D. & Kolattukudy, P. E. *Journal of Biological Chemistry* 272, 16741–5 (1997).
6. Mathur, M. & Kolattukudy, P. E. *J Biol Chem* 267, 19388–95 (1992).
7. Azad, A. K., Sirakova, T. D., Rogers, L. M. & Kolattukudy, P. E. *Proc Natl Acad Sci U S A* 93, 4787–92 (1996).

8. Cole, S. T., et al. *Nature* 393, 537–44 (1998).
9. Fitzmaurice, A. M. & Kolattukudy, P. E. *J Biol Chem* 273, 8033–8039 (1998).
10. Bystrykh, L. V., et al. *J Bacteriol* 178, 2238–44 (1996).
11. Pierce, C. H. & Dubos, R. J. *The American Review of Tuberculosis and Pulmonary Diseases* 74, 667–682 (1956).
12. Middlebrook, G., Dubos, R. J. & Pierce, C. *Journal of Experimental Medicine* 86, 175–183 (1947).
13. Rainwater, D. L. & Kolattukudy, P. E. *Journal of Biological Chemistry* 258, 2979–85 (1983).
14. Cardenas, M. E., Sanfridson, A., Cutler, N. S. & Heitman, J. *Trends In Biotechnology* 16, 427–33 (1998).
15. Neill, M. A. & Klebanoff, S. J. *Journal of Experimental Medicine* 167, 30–42 (1988).
16. Vachula, M., Holzer, T. J. & Andersen, B. R. *Journal of Immunology* 142, 1696–701 (1989).
17. Chan, J, et al. *Proceedings of the National Academy of Sciences of the United States of America* 86, 2453–7 (1989).
18. Guilfoile, P. G. & Hutchinson, C. R. *Proc Natl Acad Sci U S A* 88, 8553–7 (1991).
19. Kaur, P. *J Bacteriol* 179, 569–75 (1997).
20. Orme, I. M. *Infect Immun* 56, 3310–2 (1988).
21. Bretscher, P. A. *Immunology Today* 13, 342–5 (1992).
22. Jackson, M, et al. *Infect Immun* 67, 2867–73 (1999).
23. Bardarov, S, et al. *Proceedings of the National Academy of Sciences of the United States of America* 94, 10961–6 (1997).
24. Ochman, H., Gerber, A. S. & Hartl, D. L. *Genetics* 120, 621–3 (1988).
25. Folch, J., Lees, M. & S., S. G. H. *Journal of Biological Chemistry* 226, 497–509 (1957).
26. McAdam, R. A, et al. *Infection & Immunity* 63, 1004–12 (1995).
27. World Health Organization, World Health Report 1999.
28. Garay, S. M. in Tuberculosis (eds. Rom, W. N. & Garay, S. M.) 373–412 (Little Brown & Company, 1996).
29. Kolattukudy, et al., T. D. *Molecular Microbiology* 24, 16741–5 (1997).

All publications mentioned hereinabove are hereby incorporated by reference in their entirety. While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed is:

1. A recombinant mutant mycobacterium deficient for the synthesis or transport of dimycoserosalphthiocerol, said mycobacterium having a mutated fadD28 gene.

2. The recombinant mutant mycobacterium of claim 1 wherein the mycobacterium is selected from the group consisting of *M. tuberculosis, M. bovis*-BCG, and *M. leprae.*

3. The recombinant mutant mycobacterium of claim 2 wherein the mycobacterium is *M. tuberculosis.*

4. The recombinant mutant mycobacterium of claim 1 wherein the fadD28 gene is mutated by a method selected from the group consisting of illegitimate recombination, legitimate recombination, and transposon insertion.

5. The recombinant mutant mycobacterium of claim 4 wherein the fadD28 gene is mutated by transposon insertion.

6. A recombinant mutant mycobacterium deficient for the synthesis or transport of dimycoserosalphthiocerol, said mycobacterium having a mutated mmpL7 gene.

7. The recombinant mutant mycobacterium of claim 6, wherein the mycobacterium is selected from the group consisting of *M. tuberculosis, M. bovis*-BCG, and *M. leprae.*

8. The recombinant mutant mycobacterium of claim 7 wherein the mycobacterium is *M. tuberculosis.*

9. The recombinant mutant mycobacterium of claim 8 wherein the mmpL7 gene is mutated by a method selected from the group consisting of illegitimate recombination, legitimate recombination, and transposon insertion.

10. The recombinant mutant mycobacterium of claim 9 wherein the mmpL7 gene is mutated by transposon insertion.

11. A method of producing a recombinant mutant mycobacterium that is deficient for synthesis or transport of dimycoserosalphthiocerol, which comprises mutating a nucleic acid responsible for the synthesis or transport of dimycoserosalphthiocerol, wherein the nucleic acid responsible for the synthesis of dimycoserosalphthiocerol is fadD28 .

12. The method of claim 11, wherein the mutation is generated by a method selected from the group consisting of illegitimate recombination, legitimate recombination, and transposon insertion.

13. The method of claim 12, wherein the mutation is obtained by transposon insertion.

14. A method of producing a recombinant mutant mycobacterium that is deficient for synthesis or transport of dimycoserosalphthiocerol, which comprises mutating a nucleic acid responsible for the synthesis or transport of dimycoserosalphthiocerol, wherein the nucleic acid responsible for the transport of dimycoserosalphthiocerol is mmpL7.

15. The method of claim 14, wherein the mutation is generated by a method selected from the group consisting of illegitimate recombination, legitimate recombination and transposon insertion.

16. The method of claim 15 wherein the mutation is obtained by transposon insertion.

* * * * *